United States Patent [19]

Schäper et al.

[11] Patent Number: 5,156,041
[45] Date of Patent: Oct. 20, 1992

[54] METHOD AND APPARATUS FOR DETERMINING PERMEATION BEHAVIOR OF FOREIGN MOLECULES THROUGH SOLIDS

[75] Inventors: Siegfried Schäper, Wettstetten; Martin Winterkorn, Kösching; Hans G. Haldenwanger, Ingolstadt; Jürgen Kalus, Bayreuth; Harald Kaul, Pegnit, all of Fed. Rep. of Germany

[73] Assignee: Audi, AG, Ingolstadt, Fed. Rep. of Germany

[21] Appl. No.: 592,857

[22] Filed: Oct. 4, 1990

[30] Foreign Application Priority Data

Oct. 6, 1989 [DE] Fed. Rep. of Germany ....... 3933382

[51] Int. Cl.$^5$ ............................................. G01N 15/08
[52] U.S. Cl. ........................................ 73/38; 73/64.3; 73/64.47
[58] Field of Search ................................... 73/38, 64.3

[56] References Cited

U.S. PATENT DOCUMENTS

| | | | |
|---|---|---|---|
| 3,170,319 | 2/1965 | Karlowicz | 73/38 |
| 3,180,133 | 4/1965 | Rahme | 73/38 |
| 3,181,346 | 5/1965 | Davies | 73/38 |
| 3,286,509 | 11/1966 | Gluckman et al. | 73/38 |
| 3,902,068 | 8/1975 | Wood | 73/38 X |
| 4,112,739 | 9/1978 | Lyssy | 73/38 |
| 4,557,138 | 12/1985 | Dumitriu-Valcea et al. | 73/38 |
| 4,659,674 | 4/1987 | Bauman et al. | 73/38 |
| 4,663,969 | 5/1987 | Bibby et al. | 73/38 X |
| 4,815,316 | 3/1989 | Tantram | 73/38 |
| 4,862,730 | 9/1989 | Crosby | 73/38 |

FOREIGN PATENT DOCUMENTS 1213384 2/1986 U.S.S.R. ............... 73/64.3

OTHER PUBLICATIONS

Gobrecht, Professor Dr. Ing. H, Lehrbuch der Experimental Physik, 1975, pp. 426–450.

Primary Examiner—Hezron E. Williams
Assistant Examiner—Joseph W. Roskos
Attorney, Agent, or Firm—Jacques M. Dulin; Thomas C. Feix

[57] ABSTRACT

Methods and apparatus for determining the permeation behavior of foreign fluid molecules into solids whereby the results are typically obtained in less than one day. In a principal embodiment, information about the relationship between the saturation concentration and the diffusion constant of the solid is obtained by subjecting a first, thick, sample of the solid to the foreign fluid substance, which has been radioactively-tagged with a class C isotope, for a short diffusion time interval. The penetrated foreign substance is then washed out of the thick sample with an untagged solvent and the resulting solution is then analyzed to determine the quantity of the foreign substance that has diffused into the thick sample for the diffusion time. A second, thin, sample of the solid is prepared, and analyzed in a series of steps analogous to the thick, sample, whereby information concerning the saturation concentration, individually, is obtained. The above results are then used to determine the diffusion flow rate of the fluid substance through the solid. An alternative method determines the permeation behavior of a two-layer solid where each layer has a different solubility. The alternate embodiment provides for an apparatus to isolate an exposed surface of the second thicker layer so that diffusion parameters of the second thicker layer may be determined independently of the first layer.

24 Claims, 1 Drawing Sheet

METHOD AND APPARATUS FOR DETERMINING PERMEATION BEHAVIOR OF FOREIGN MOLECULES THROUGH SOLIDS

FIELD

The invention relates generally to methods and apparatus for determining the permeation properties of foreign molecules through solids. More particularly, the invention relates to methods and apparatus for determining the permeation properties of foreign molecules through solids whereby the results are obtained by measuring the amount of the substance that diffused into the solids during a short time without waiting for a complete diffusion of the liquid through the solid to find a value for the diffusion flow rate.

BACKGROUND

There are many methods that are used to determine the permeation properties of molecules through solids. These methods are based on measuring the amounts of substance that has already diffused through the solid. This diffused quantity can be determined by one of two ways. The first way the diffused quantity can be determined is by a measurement of the weight loss of the diffusing substance in a sealed container both before and after the diffusion. This first method does not yield entirely complete results because it is not particularly sensitive. The second method involves isolating and capturing the diffused substance and determining its quantity. While this method provides significantly better results than the first method, both methods are very time consuming. Because the diffusion process of molecules through solids is a very slow process, the measurement procedure by these methods can last for several days or even weeks.

Various alternatives have been taken to bypass these long measurement periods. For instance, one alternative involves using a thin membrane as a solid (such as a micro-tome section) and using a material that diffuses very quickly as the diffusing substance. However, this alternative has its difficulties since the thin membrane solid is difficult to prepare on thin-walled solids. Additionally, the substitution of a quickly diffusing material for the actual diffusing substance restricts the validity of the test.

Thus, there is a need in the art for a method to determine the permeation behavior of molecules through solids whereby the measured results are quickly obtained and are highly accurate. There is also a need in the art for a method to determine the permeation properties for foreign molecules into solids while the diffusing substance is still being diffused through the solid. There is also a need in the art for a method to determine the permeation behavior of molecules through a 2 layer solid where the thickness of each layer is unknown.

THE INVENTION

OBJECTS

It is among the objects of the invention to provide methods and apparatus for determining the permeation behavior of foreign molecules through solids whereby the measured results are usually obtained in less than 1 day.

It is another object of the invention to provide methods and apparatus for greatly decreasing the time normally required for determining the permeation behavior of foreign molecules through solids by preparing thick and thin samples of the solid and subjecting both samples to relatively short diffusion times whereby the amount of the foreign substance diffused therein is recovered through a solvent washout process and the resulting solution is analyzed to determine the saturation concentration and the diffusion constant of the solid.

It is another object of the invention to provide a method for determining the permeation behavior of foreign molecules through solids by tagging the diffusing substance with a radioactive isotope in order to determine, with greater sensitivity, the amount of the substance that has diffused into the solid after a certain time interval by measuring the radioactivity present in the recovered solution.

It is yet another object of the invention to provide a method for determining the permeation behavior of foreign molecules through a two-layer solid, each layer having different solubility characteristics, wherein one layer is a thin coating or treatment to inhibit diffusion of foreign substances into the second layer.

Still other objects of the invention will be evident from the specification and drawings

DRAWINGS

The invention is illustrated in more detail by reference to the drawings in which.

SUMMARY

Figure 1:
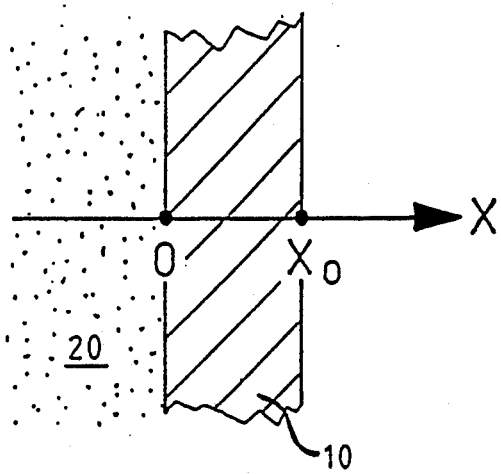
FIG. 1 is a schematic showing the diffusion of liquid molecules through one side of a homogenous solid (shown in cross-section).

The method of this invention provides for the determination of the diffusion parameters of foreign molecules through solids. One application of the invention is the determination of the diffusion parameters of gasoline into a plastic-walled fuel container. The permeation behavior is observed in this method by causing a penetration of gasoline molecules into the solid plastic wall by means of appropriate surface contact and then determining the quantity of gasoline molecules that have diffused into the solid in a specified time.

The formula used to determine the diffusion flow is:

$$\frac{dn}{dt} = \frac{-D \cdot F \cdot c_o}{X_o} \quad (1)$$

Where:
dn/dt = Diffusion flow rate (particles/s)
D = Diffusion constant ($cm^2/s$)
F = Surface area ($cm^2$)
$c_o$ = Concentration of diffusing substance at the wetted side of the solid (particles/$cm^3$)
and $X_o$ = Thickness of the solid (centimeters)

The unknown variables in the governing formula for determination of the diffusion flow are the saturation concentration $c_o$ and the diffusion constant D. These variables are necessary for finding the quantity of the penetrated substance S.

Unlike current methods used for determining the quantity of the penetrated substance S which provide for a measurement of the penetrated substance after complete diffusion has taken place (sometimes lasting up to days or even weeks), the method of this invention determines the permeation behavior over relatively short diffusion times (i.e., on the order of 5–100 minutes) and all the desired information concerning the permeation behavior is obtained usually within one day (24 hours). For sufficiently small diffusion times, the quantity of the penetrated substance is derived from the formula:

$$S(t_d) = 2 \cdot F \cdot c_o \cdot \sqrt{\frac{D \cdot t_d}{\pi}} , \text{ where} \tag{2}$$

$S(t_d)$ is the quantity of the penetrated substance; and $t_d$ is the time for diffusion.

The first part of the method solves for the unknown variables of the product of the saturation concentration $c_o$ and the square root of the diffusion constant D by a five step process which includes the steps of:
1) preparation of a surface element of the solid and treating the solid as infinitely thick,
2) introducing the foreign fluid molecules into contact with one surface of the solid,
3) removing the foreign molecule material from the surface of the solid after a short diffusion time of about 5–100 minutes,
4) Washing out the substance of the foreign molecules as diffused into the solid, and
5) determining from the washout solution the quantity of the substance of foreign molecules that has diffused into the solid by mass spectrometry or like analytical techniques for identifying the intensity distribution of masses.

The second part of the method also solves for the determination of the saturation concentration $c_o$ individually by a similar five step process which includes the steps of:
1) preparation of a micro-tome section of a surface element of the solid so that after a short diffusion time a complete saturation of the diffusing foreign molecules will take place,
2) introducing the micro-tome section of the solid into contact with the foreign fluid molecules,
3) removing the foreign molecule substance from the surface of the micro-tome section after a saturation time of about 1 hour,
4) washing out the substance that diffused in,
5) determining from the washout solution the quantity of material that has diffused into the solid by mass spectrometry or like analytical techniques for identifying the intensity distribution of masses.

In the preferred best mode, the foreign fluid molecules are radioactively-tagged prior to introduction to the solid sample. After the foreign fluid molecules have been washed out from the sample, a scintillation counter is used to determine the quantity of the foreign substance that has diffused into the solid by measuring the number of radioactive decays per unit time in the washout solution.

Where the diffusion of gasoline through plastic is observed, the step of radioactively tagging the foreign molecules substance (gasoline) is simplified, since the hydrocarbons in gasoline are by their nature easily radioactively taggable with carbon 14. Thus, the determination of the quantity of the substance is easily found after a "washout" from the solid by determining the amount of radioactivity remaining in the solution.

An alternate method of this invention provides for the determination of the diffusion parameters in a one side wetted, two-layer foreign body where the exposed first layer is clearly thinner than the non-exposed second layer and the foreign molecules in the first layer have a lower solubility than in the second layer. A specific application of this method may be used to determine the permeation behavior of gasoline molecules through a interior-fluorinated or interior-sulfonated plastic-lined fuel container. Since the thickness of the lining of the first layer is insignificant relative to the thickness of the wall of the fuel container, the thickness of the thin layer and its associated diffusion constant can be ignored. Thus, the governing formula for the diffusion flow rate through this type of two-layer solid simplifies to:

$$\frac{dn}{dt} = \frac{c_o^1 \cdot D_2}{L} \tag{7}$$

Where: $dn/dt$ = Diffusion flow rate (particles/s)

$c_o^1$ = Concentration at the Surface at the first layer in solid $D_2$ = Diffusion constant of the second layer, and $L$ = Thickness of the second layer.

As is the case for a homogeneous solid, the diffusion constant for the thicker solid $D$, is ascertainable by the five step method of the invention. Special care is taken to isolate the air exposed side of the thicker solid for diffusion purposes, as it is this side that is to be taken into the evaluation.

Thus, the method of this invention makes possible the determination of the diffusion parameters where only about one day will pass from preparation of the sample until the results are obtained. The method also simplifies the handling and sample preparation procedures for determining diffusion parameters of fluids into solids. The quantities of the radioactivity used in the methods are small, typically about $2\mu$ Ci, and the diffused radioactivity is very small, usually less that $0.01$ $\mu$ Ci. For the gasoline into plastics application, the measurements are taken in a class-c isotope laboratory having equipment for $C^{14}$ measurements. Several measurements may be conducted in parallel due to the relatively simple apparatus involved.

DETAILED DESCRIPTION OF THE BEST MODE

The following detailed description illustrates the invention by way of example, not by way of limitation of the principles of the invention. This description will clearly enable one skilled in the art to make and use the invention, and describes several embodiments, adaptations, variations, alternatives and uses of the invention, including what we presently believe is the best mode of carrying out the invention.

As is seen in FIG. 1, a schematic of a solid 10 is shown in cross-section. By way of example only, the solid 10 here is formed by the wall of a plastic fuel tank. It is understood that the solid may be any other material for which information about the diffusion flow rate of particular fluid molecules through the solid is sought. The solid 10 is bounded on one side (hereinafter referred to as the "wetted side") by a liquid 20. In this illustration the fluid is gasoline, but it is understood that it may any other fluid for which information about its permeation behavior through a solid is desired.

In an aid to understand the formulas that will be presented below, an X axis is oriented perpendicular to the wall of the solid 10 and runs in the thickness direction of solid 10. Hence, the 0 point is set at the surface of the wetted side and designated as 0 and $X°$ represents the thickness of solid 10.

By way of illustration only, the measuring principal of the invention will be described using the diffusion of constituents of gasoline into plastic. The diffusion flow rate through the solid under stationary diffusion is the quantity of final interest and is found from the following formula:

$$\frac{dn}{dt} = \frac{-D \cdot F \cdot c_o}{X_o} \quad (1)$$

Since the surface area F of the test area and thickness of the solid $x_o$ are directly accessible quantities, we need to determine the concentration of diffusing substance at the wetted side of the solid $c_o$ and the diffusion constant D. By using a measurement method that determines the quantity of the diffused substance, the variables D and $c_o$ can be obtained directly from the above formula (1). However, to determine the variables D and $c_o$ in a short time, one can not wait until a constant diffusion flow to the solid 10 has set in. Thus, it is desirable to determine how much liquid has diffused into the solid from the time of wetting at $t=0$ until a time t some minutes later. The difficulty here is to ascertain D and $c_o$ from the diffused quantity of material.

Since the diffusion process is so slow, the solid can be viewed as infinitely thick for very short periods of time. Thus, an equation can be set up with a diffused quantity of material for very small time periods.

The following boundary conditions apply for the concentration of the substance that is being diffused through the solid 10:

$c(x)=0$ for $t<0$ $c(x=0)=c_o$ for $t \geq 0$.

The equation for the diffused quantity of material is S is represented by the integral:

$$S(t) = F \int_0^\infty c(x, t) \, dx.$$

For sufficiently small diffusion times, the following expression is obtained:

$$S(t_d) = 2 \cdot F \cdot c_o \cdot \sqrt{\frac{D \cdot t_d}{\pi}} \quad (2)$$

Thus, the diffused quantity of material S varies as a square-root relation with regard to the diffusion time $t_d$.

Accordingly, by obtaining a measurement of the quantity of liquid diffused in a short time, we obtain information about the quantity $c_o \cdot \sqrt{D}$. However, we still need information concerning the quantity $c_o \cdot D$ to solve for the diffusion flow rate of equation (1). Thus, additional information is required.

One approach in accord with this invention to obtain the additional information is to determine $c_o$ individually. Accordingly, the measurement method to determine the diffusion parameters of a liquid in a homogeneous solid is organized essentially into two parts. Part one involves the determination of the product ($c_o \cdot \sqrt{D}$). The second part involves the determination of $c_o$ individually.

For this two-part procedure the diffusing liquids are radioactively tagged. This enables detection with a high degree of sensitivity. This procedure works particularly well for measuring the permeation behavior of gasoline into the plastic-walled fuel tanks or the like, as the constituents of commercially available gasoline (i.e. hydrocarbons), are easily taggable with $C^{14}$. $C^{14}$ is a beta-emitter with an average beta energy of $E=47keV$ and a maximum beta energy of $E_{max}=156keV$. This energy is so small that detectors intended for measurement of this radiation should have windows with a mass coverage of less than 1 mg/cm$^2$. If $C^{14}$-tagged substances diffuse into a solid, the solid itself serves as a shelf for very small penetration depths. Thus, only the radioactivity at the surface can be detected. Therefore it is necessary to dissolve out the diffused liquid (gasoline) from the solid (plastic fuel tank wall) and then to determine the radioactivity of the solution.

In practice the method for the determination of ($c_o \cdot \sqrt{D}$) is as follows:

1. Preparation of the Sample

First a disk shape of the sample material (e.g. plastic fuel tank wall) is cut to size. The disk should be thicker than 1 mm so that for short diffusion times, the material can be viewed as infinitely thick. The surface of the dish should be greater than 0.5 cm$^2$ so that boundary effects do not affect the result too much. The sample surface should be cleaned and dried so that any liquid that may have previously penetrated into the sample is effectively removed.

2. Diffusion

The sample is placed into the radioactively-tagged liquid (i.e. gasoline) for the diffusion time t (hereinafter referred to as "$t_d$"). It is found that the radioactivity level of the liquid in the neighborhood of 1 $\mu$Ci/ml is entirely sufficient for a proper measurement. It is also found that suitable diffusion times lie between 5 and 100 minutes. The length of the time for diffusion will vary with the thickness of the sample.

For ease of handling, $t_d$ should be at least 5 minutes in order to separate the diffusing step from the initial surface cleaning in the washout step below. Hence, the diffusion time $t_d$ required for good results is relatively short. The length of time, $t_d$, is dependent on the thickness $x_o$ of the solid sample. As a rule of thumb, diffusion times should be smaller than $x_o^2/D$. In the example of diffusing gasoline into plastics, time intervals less than 60 minutes provide good results.

Care should be taken to insure that the sample is fully wetted for an adequate reading. Moreover, the vessel should not be much larger than the sample so that the use of radioactive liquid is kept to a minimum.

3. Washout

After the desired diffusion time has elapsed, the sample material is removed and subjected to a multi-step washing process. The first step involves placing the sample material for a brief emersion in a non-radioactive liquid. The time period for this first washing should be very short compared to the diffusion time so that the diffused liquid is not washed out of the solid, as this is to be done in the actual washout process. The first step merely removes residual radioactive liquid from the surface of the sample.

The second step involves the actual washout process whereby the liquid that has diffused into the solid sample material is washed out of the solid and made accessible for measurement. In this step the sample is placed within a vessel filled with an untagged solvent. It is important that the diffused liquid be highly soluble in the solvent and that the volume of the solvent be at least twice as great as the volume of the sample. In addition, the actual washout time ("$t_{wash}$" or "$t_w$") should be greater (at least 10 times greater) than the diffusion time. Under these conditions, one may assume that the majority of the diffused liquid has diffused out again and is essentially entirely replaced by the untagged solvent.

Scintillation

A scintillation counter is used for the determination of beta radioactivity with the solution. To do this, the radioactive liquid must be mixed with a scintillator. For this purpose it has been found that Rotiszint-11, a toluol-based scintillator, may be used to make a suitable scintillation cocktail. While Rotiszint-11 is the preferred scintillation cocktail for use in determining the permeation behavior of gasoline molecules through a plastic solid, it is understood that any methylbenzene or phenylmethyl based scintillators will work provided that they are soluble in high-octane gasolines. If the diffused liquid is highly soluble in the scintillation cocktail, then the scintillation cocktail can also be used for the washout.

5. Evaluation

The scintillation counter is used to measure the quantity of $S'(t_d)$ (or more simply "$S'$"), where $S'$ is the activity or the number of radioactive decays (or clicks on the scintillation counter) per time unit of the sample after the radioactively marked liquid has diffused into the solid sample for diffusion time $t_d$. The quantity of the sample $S(t_d)$ can be determined from the activity reading of the scintillation counter by the relation:

$$S(t_d) = S'/A_{spez}$$

where $A_{spez}$ is the specific radioactivity of the diffused liquid (in cps/cm$^3$; where cps=1/s). Thus from equation (2) we have:

$$c_o \cdot \sqrt{D} = \frac{S' \cdot \sqrt{\pi}}{2F \cdot A_{spez} \cdot \sqrt{t}} \quad (3)$$

The second part determination of $c_o$ is analogous to the above described 5-step method for the determination of the quantity $c_o \cdot \sqrt{D}$, except the sample must be very thin (about 20 μm) and the diffusion time must be relatively long (roughly about 1 hour). In this second part determination for $c_o$, the diffusion time for this procedure is actually the time required for a complete saturation of the microtome section of the solid and is hereafter referred to as "$t_s$" or "$t_{saturation}$". By using a microtome-section of the solid sample and very long saturation times, one may assume that a uniform saturation concentration, $c_o$, is now reached throughout the thickness of the sample. The saturation concentration $c_o$ is then obtained from the following equation:

$$c_o = \frac{S''}{V \cdot A_{pez}} \quad (4)$$

where, V is the volume of the thin sample; and
$S''$ is the activity of the sample used for measuring the concentration of saturation $c_o$. V can be determined by weight when the density of the sample is known. The value for $S''$ is read directly off the scintillation counter and is not dependent on the time for saturation t if the saturation time is long enough for a complete saturation. In other words, as in washout procedure in step 3 for the solid sample, $t_w$ for the thin sample must be at least ten times as long as t (i.e., approximately 10 hours) to insure that the majority of the saturated fluid is removed from the thin sample and entirely replaced by the solvent.

It follows then that by combining equations (3) and (4) we have:

$$\sqrt{D} = \frac{\sqrt{\pi} \cdot V \cdot S'}{2F \cdot S'' \cdot \sqrt{t_d}} \quad (5)$$

The value for the saturation concentration, $c_o$, obtained from equation (4) and $\sqrt{D}$ obtained in equation (5) are now used to determine the diffusion flow rate according to the first equation (1)

$$\frac{dn}{dt} = \frac{-D \cdot F \cdot c_o}{X_o}$$

Thus, by using very short diffusion times, $t_d$, to solve for the quantity ($c_o \cdot \sqrt{D}$) and slightly longer saturation times, $t_s$, to solve for $c_o$, individually, all the desired permeation behavior of the foreign fluid molecules into the solid sample is known is less than 1 day.

For example, in the case of determining the permeation behavior of gasoline into plastics, we may have a diffusion time, $t_d$, for the thick solid sample in the range of 5-100 minutes. The washout time $t_w$ associated with the thick sample diffusion will be at minimum ten times as great as $t_d$, and will be in the range of 50-1,000 minutes (50 min-16 hours:40 min). The saturation time, $t_s$, for the thin sample will be around 1 hour, and the associated washout time $t_w$ for the thin sample saturation will be around 10 hours. Thus, for most cases the permeation behavior of gasoline diffusing into a homogenous solid plastic fuel container is obtained within the range of 11 hours:55 minutes to 28 hours:20 minutes when both measurements for the thick and thin samples are conducted sequentially.

DETERMINATION OF DIFFUSION PARAMETERS OF LIQUID IN TWO-LAYER SOLID

Figure 2:
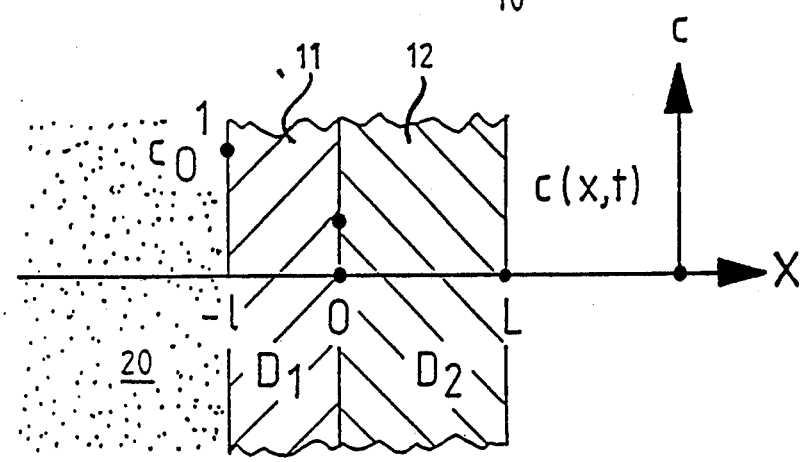
FIG. 2 is a schematic illustration showing the diffusion of liquid molecules through one side of a two layer solid (shown in cross-section).

Referring now to FIG. 2, the above described 5-step method for determination of the diffusion parameters $c_o$ (saturation concentration) and D (the diffusion constant) for a single layer (homogeneous) solid is also applicable for the determination of these diffusion parameters for a two-layer solid. For our purposes, an example of such a two-layer solid may be formed as an interior-fluorinated or interior-sulfonated plastic fuel container.

If certain prerequisites are met, then the relative parameters can be determined even for solids having a surface treatment or coating in order to reduce diffusion. As best seen in FIG. 2, both solids 11 and 12 are shown in cross-section, whereby a first layer 11 represents the coating that is wetted on one side (i.e. the side exposed to liquid 20) and has a saturation concentration of $c^1_o$.

As a point of reference for the following discussion we designate a 0-point as the separation point between layer 11 and layer 12. Thus, layer 11 (i.e. the sulfonated or fluorinated layered coating) has a thickness of 1, and the solid layer 12 has a thickness of L. The thickness of each solid is designated along the x-axis as before, while the C-axis represents the concentration of diffusing liquid at any time, t, through the solid. In general, as expected, the concentration drops along the cross-section through the wall as the diffusing liquid travels from the initial point $-1$ to the ending point L.

The following assumptions and definitions are used for the present case:
1. Layer 11 has a diffusion constant $D_1$ and a concentration $c1 = c2(x,t)$ in the region between $x = -1$ and $x = 0$.
2. Layer 12 has a diffusion constant $D_2$ and a concentration $c2 = c2(x,t)$ in the region between $x = 0$ and $x = L$.
3. L is much greater (i.e. thicker) than 1; and the boundary condition is $L \to \infty$
4. There is no contact diffusion resistance at the interface at $x = 0$.
5. The solubility in substance 2 (i.e. the second layer or element 12 of FIG. 2) is greater than in substance 1 (i.e. the first layer or element 11 in FIG. 2).

Thus, the following boundary conditions apply:

$c1(x,t)$ $c2(x,t) \neq 0$ for $t < 0$ $c1(-1,t) = = c^1_o$ for $t > 0$ $c1(0,t) = c2(0,t)$ for $t > 0$ For stationary diffusion the following expression is obtained with the quantity of material $dn/dt$ diffusing per second and per $cm^2$ (i.e., per surface area):

$$\frac{dn}{dt} = \frac{c_o^1}{\frac{L}{D_2} + \frac{1}{D_1}} \quad (6)$$

From the above equation (6) we see that for two-layer solids it is better if $c^1_o$ (i.e. the solubility of the first layer), is small. That is, a smaller solubility limit for the first layer, (i.e. the layer in contact with the diffusing fluid), means that the rate of diffusion is very slow. This is desirable, for instance, in a solid container such as a gas tank containing gasoline. Equation (6) is greatly simplified if 1 is much smaller (i.e., thinner) than L, in which case the quantity $(1/D_1)$ can be ignored. The relation would then read as follows:

$$\frac{dn}{dt} = \frac{c_o^1 \cdot D_2}{L} \quad (7)$$

This would be the normal case for an interior-chlorinated or interior-sulfonated plastic fuel containers where 1 is the thickness of the surface treatment layer (i.e., element 11 of FIG. 2) and L is the thickness of the plastic fuel tank wall (i.e., element 12 of FIG. 2).

As before, the diffusion equation for a two-layer solid has been simplified to the unknown variables of the saturation concentration $c^1_o$ and the diffusion constant $D_2$. However, these parameters are not as readily accessible as they are for a homogenous solid as in FIG. 1.

While both the diffusion constant, $D_2$, and saturation concentration, $C_o^2$, can be determined in an analogous manner to the diffusion constant, $D$, and saturation concentration, $c_o$, for homogenous solids (i.e. see discussion of FIG. 1), care must be taken that only the second surface (i.e. the air exposed surface of solid 12 of the second layer 12) be wetted during the thick sample diffusion and their sample saturation and that only this surface is taken into the evaluation. A special apparatus (see FIG. 3) may be used for wetting only one surface of solid layer 12.

Figure 3:
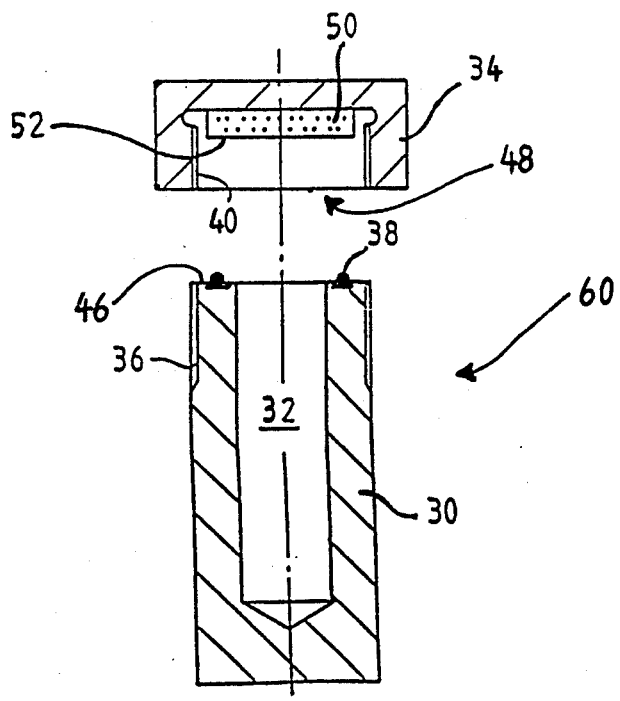
FIG. 3 is a side elevation view of an apparatus for isolating one side of a solid for liquid molecule diffusion test purposes.

Referring now to FIG. 3, the wetting of only one surface of layer 12 can be achieved by placing the sample 50 (i.e. the two-layer solid) between cover 34 and cylindrical vessel 30 of a bottle 60. The vessel 30, which is preferably made of brass, has an interior cavity 32 and has at its upper end 42 an opening 44. The cylindrical vessel 30 is also provided with outer threading 36 adjacent the upper end 42 along the outer wall of the vessel 30. O-ring 38 is also provided along the top wall 46 of vessel 30 to form a gasket or seal against the lower surface of sample 50 when sample 50 and the attached cover 34 are placed over the upper end 42 of vessel 30.

The cover 34 has internal threads 40 disposed along its inner wall adjacent its lower opened end 48. The internal threads 40 cooperate with the outer threads 36 of vessel 30 to secure cover 34 to vessel 30. The preferred materials for construction of the cover 34 are aluminum.

In use, the sample (i.e., the 2 layer solid of FIG. 2) is first placed, layer 11 side down within cover 34 before cover 34 is screwed on to vessel 30, thus forming a sealed contact between sample 50 and O-ring 38. By placing the sample 50 within this apparatus and securing it in the above described manner, any liquids within cavity 32 of vessel 30 can only come into contact with the lower surface 52 of sample 50. For our purposes, the lower surface 52 of sample 50 would correspond to the exposed surface of solid layer 12 at point $X = L$ of FIG. 2.

The steps of cleaning and washout of a two-layer solid are similar to that as described above in connection with the homogenous solid as described with reference to FIG. 1.

Referring back to FIG. 2, the saturation concentration $c^1_o$ can not be obtained with the method described above, since no microtome section can be made of solid layer 11 due to its small thickness 1. However, because of the negligible thickness of 1 as compared to the thickness of L, it may be assumed that the saturation concentration of c1 (i.e. the final saturation concentration of layer 11) will be approximately equal to $c^1_o$ (i.e. the initial saturation concentration at the wetted side of layer 11) after a relatively short diffusion time, $t_d$. In this situation, further diffusion of the liquid 20 into layer 12 occurs analogous to the above described diffusion condition of FIG. 1 relating to a homogenous solid with the exception that the boundary condition c2 (0,t) is approximately equal to $c^1_o$.

Thus, solving for the quantity of material S, for the diffusion due to the wetting of only the one surface layer 11 we have:

$$S_1 \approx 2 \cdot F \cdot c_o^1 \cdot \left[ \sqrt{\frac{D_2 \cdot t}{\pi}} + \frac{1}{2} \right] \tag{8a}$$

And for diffusion out from the surface layer 12 we have the following relation:

$$S_1 \approx 2 \cdot F \cdot c_o^2 \cdot \sqrt{\frac{D_2 \cdot t}{\pi}} \tag{8b}$$

For sufficiently long diffusion times $t_d$, we have:

$$\sqrt{\frac{D_2 \cdot t}{\pi}} >> \frac{1}{2}$$

The influence of the thin layer 11 can then be neglected (i.e. the expression $\frac{1}{2}$ is insignificant relative to the expression of $(D_2 \cdot t)/\pi$ in equation (8a)). If the same diffusion times, $t_d$, are used in equations (8a) and (8b), then $S_1$ varies with respect to $S_2$ as $c^1_o$ varies with respect to $c^2_o$. Thus, by measuring the quantity diffused in from the surface of layer 11 we can then compute $c^1_o$ from the following expression:

$$c_o^1 = \frac{c_o^2 \cdot S_1}{S_2} \tag{8a}$$

Thus, all the diffusion parameters ($D_2$, $c^2_o$ and $c^1_o$) in a 1-side wetted, 2-layer solid body are now ascertainable. That is, the diffusion constant $D_2$ can be found by the 5 step thick sample method used for the homogenous solid as described with reference to FIG. 1. Similarly, the saturation concentration, $c_o$, is ascertained by the 5 step thin sample or microtome section method for a homogeneous solid. The concentration at the surface of the first layer in the solid, $c^1_o$, is ascertained from equation (8a) and the diffusion flow of the two-layer solid is ascertainable by using these above determined values for $D_2$, $c^1_o$, and $c_o$, in equation (7) with L being taken as the entire thickness of the solid sample, 1+L. In the alternative, a more exact determination of L can be made by measuring L with a micrometer.

It should be understood that various modifications within the scope of this invention can be made by one of ordinary skill in the art without departing from the spirit thereof. We therefore wish our invention to be defined by the scope of the appended claims as broadly as the prior art will permit, and in view of the specification if need be.

We claim:

1. A method to-determine the permeation behavior of foreign molecules in solids, comprising the steps of:
   a) directly contacting the surface of the solid having at least one plastic layer with the foreign molecules for a time sufficient to effect penetration of the solid by the foreign molecules; and
   b) determining the quantity of foreign molecules that diffuse into said solid.

2. A method of determining the permeation behavior in terms of the diffusion flow rate as in claim 1 wherein:
   a) said step of determining the quantity of foreign molecules includes:
      i) determining the surface area of the solid;
      ii) determining the thickness of the solid;
      iii) determining the quantity of foreign molecules penetrating the solid; and
      iv) determining the diffusion flow rate dn/dt in accord with the formula:

$$\frac{dn}{dt} = \frac{-D \cdot F \cdot c_o}{X_o}, \text{ where}$$

$dn/dt$ = Diffusion flow rate;
$D$ = Diffusion constant;
$F$ = Surface area;
$c_o$ = Concentration of the substance diffused into the solid at the exposed side of the solid; and
$X_o$ = Thickness of the solid.

3. A method of determining the permeation behavior as in claim 2 wherein:
   a) the step of determining the quantity S(t) of foreign molecules penetrating the solid in a given time, t, is in accord with the formula:

$$S(t) = F \int_0^\infty c(x, t) \, dx; \text{ and}$$

b) for sufficiently small diffusion times the value s(t) is in accord with the formula:

$$S(t) = 2 \cdot F \cdot c_o \cdot \sqrt{\frac{D \cdot t}{\pi}} \; ;$$

and which includes the step of:
   c) determining the quantities of $(c_o \cdot \sqrt{D})$ and $c_o$, to obtain the quantities of $c_o$ and D, where c (x,t) is the location and time-dependent concentration of the diffusing substance.

4. A method of determining the permeation behavior as in claim 3 wherein:
   a) the step of determining $(c_o \cdot \sqrt{D})$ includes:
      i) preparation of a surface element of the solid that can be viewed with sufficient accuracy as infinitely thick;
      ii) contacting the surface of the solid with the foreign molecules for a time, t;
      iii) removal of residual foreign molecule substance from the surface after a specified time, t;
      iv) washing out the foreign molecules diffused into the solid; and
      v) determining the quantity of foreign molecules that diffused into the solid.

5. A method of determining the permeation behavior as in claim 4 wherein:
   a) the step of determining of $c_o$ includes:
      i) preparation of a surface element of the solid that is sufficiently thin, so that after a short diffusion time a saturation of the diffusing foreign molecules into the solid occurs;
      ii) contacting the surface with the foreign molecules for a time t,
      iii) removal of residual foreign molecule substance from the surface after a specified time, t;
      iv) washing out the foreign molecules diffused into the solid; and v) determining the quantity of foreign molecules that diffused into the solid.

6. Method of determining the permeation behavior of a fluid through a solid comprising the steps of:
  a) preparing a first and a second sample of said solid, said first sample being substantially thicker than said second sample;
  b) contacting each of said samples with said fluid for a time, t, said time of contact with said first, thick, solid sample being shorter than the time of contact with said second, thin, solid sample;
  c) recovering fluid that has absorbed or diffused into each of said solid samples during their respective times of contact;
  d) determining the saturation concentration in relation to the amount of fluid recovered from said second, thin, sample;
  e) determining the diffusion constant in relation to the amount of fluid recovered from said first, thick, sample; and
  f) determining the diffusion flow rate of said solid based on the diffusion constant and saturation concentration.

7. Permeation behavior determination method as in claim 6 wherein:
  a) each of said samples is contacted by said fluid over the same amount of surface area.

8. Permeation behavior determination method as in claim 7 wherein:
  a) said thick sample is above about 500 times thicker than said thin sample; and
  b) said contact time for said thin sample is less than about 12 times longer than the contact time for said thick sample.

9. Permeation behavior determination method as in claim 8 wherein:
  a) said fluid is recovered by washing with a solvent, the wash time of which is at least 10 times longer than said contact time.

10. Permeation behavior determination method as in claim 9 wherein:
  a) said fluid is tagged for analysis.

11. Permeation behavior determination method as in claim 10 wherein:
  a) said tag is a radioactive tag and the amount of fluid recovered is determined by counting in a scintillation counter.

12. Permeation behavior determination method as in claim 11 wherein:
  a) said fluid is a liquid.

13. Permeation behavior determination method as in claim 12 wherein:
  a) said liquid is gasoline; and
  b) said solid is plastic.

14. Permeation behavior determination method as in claim 6 wherein:
  a) said solid is a multi-layer solid.

15. Permeation behavior determination method as in claim 14 wherein:
  a) the layers are of differing thickness and the samples are prepared from at least the thicker layer.

16. Permeation behavior determination method as in claim 15 wherein:
  a) the solid is a plastic fuel tank having a fluorinated or sulfonated plastic inner layer which is the second, thinner, layer;
  b) said liquid is $C^{14}$-tagged gasoline.

17. Analytic method for determining the unknown variables of the concentration saturation $c_o$ and the diffusion constant D for use in determining the diffusion flow rate, dn/dt, of foreign fluid molecules into solids comprising the steps, in any sequence, of:
  a) preparing a surface of a first, thick, sample of surface area F of the solid so that residual amounts of said foreign fluid molecules are substantially, entirely removed;
  b) tagging the foreign fluid with a radioactive isotope;
  c) contacting one surface of said prepared first, thick, sample with the radioactively-tagged foreign fluid for a short diffusion time, $t_d$, to permit said radioactively-tagged foreign fluid to diffuse into said first, thick, sample;
  d) recovering said fluid that has permeated into said first, thick, sample by washing with solvent for a long wash time, $tw_1$, to obtain a first fluid/solvent mixture, said wash time for said first thick sample being at least ten times that of said diffusion time, $t_d$;
  e) determining the amount of the diffused substance S that has been recovered by measuring the radioactivity present in the recovered first fluid/solvent mixture;
  f) determining the quantity $c_o \cdot \sqrt{D}$ in accord with the equation:

$$C_o \cdot \sqrt{D} = \frac{S' \cdot \sqrt{\pi}}{2 \cdot F \cdot A_{spez} \cdot \sqrt{t_d}}, \text{ wherein}$$

i) S' is the radioactivity, in radioactive decays per unit time, present in the recovered first fluid/solvent mixture which is representative of the foreign fluid that diffused into the first, thick, solid sample during the diffusion time $t_d$, and
  ii) $A_{spez}$ is the specific radioactivity of the diffused fluid;
  g) preparing an ascertained volume of a second, thin, sample of surface area F of the solid so that residual amounts of said foreign fluid molecules are substantially entirely removed;
  h) contacting said prepared second, thin, sample of said solid with said radioactively-tagged foreign fluid for a long saturation time, $t_s$, to permit said second, thin, sample to become saturated by said foreign fluid;
  i) recovering said radioactively-tagged fluid that has saturated said second, thin, sample by washing with solvent for a long wash time, $tw_2$, to obtain a second fluid/solvent mixture, said wash time for said second, thin, sample being at least ten times that of said saturation time, $t_s$;
  j) determining the saturation concentration $c_o$ of said second, thin, solid sample by measuring the radioactivity present in the recovered second fluid/solvent mixture;
  k) determining $c_o$ in accord with the equation:

$$c_o = \frac{S''}{V \cdot A_{spez}}, \text{ wherein:}$$

i) S'' is the radioactivity, in radioactive decays per unit time, present in the recovered second fluid/solvent mixture which is representative of the foreign fluid that saturated the second, thin, sample during the saturation time, $t_s$; and ii) V is said volume of the second, thin, sample;

l) determining D from the above-determined value of $c_o$;

m) determining dn/dt according to the formula:

$$dn/dt = (-D \cdot F \cdot c_o)/x_o,$$

wherein:

i) F is said surface area of said solid, and ii) $x_o$ is the thickness of a sample of the solid, the diffusion flow rate of which is desired to be known.

18. Analytic method as in claim 17 wherein:

a) a class-C isotope is used for radioactively-tagging said foreign fluid substance;

b) the quantity of radioactivity used in said method is in the range of about 1-3 $\mu$Ci; and c) the quantity of the radioactivity diffused during the practice of said method is in the range of about 0.002-0.015 $\mu$Ci.

19. Analytic method as in claim 18 wherein:

a) said foreign fluid substance is gasoline;

b) said solid is homogenous plastic; and c) said class-C isotope is $C^{14}$.

20. Analytic method as in claim 19 wherein:

a) the thickness dimension of said first, thick, sample is at least as great as 1 mm;

b) the length of said diffusion time, $t_d$, for said first, thick, sample is in the range of about 5-100 minutes;

c) the thickness dimension of said second, thin, sample is in the range of about 15 $\mu$m to 50 $\mu$m; and d) the length of said saturation time, $t_s$, for said second, thin, sample is in the range of about 45 minutes to 90 minutes.

21. Analytic method as in claim 20 wherein:

a) said wash time, $tw_1$, for said first, thick, sample being long enough to substantially, entirely remove all of said $C^{14}$ tagged gasoline molecules that have diffused into said first, thick, sample whereby said long wash time, tw , being in the range of about 50 minutes to 16 hours and 40 minutes;

b) said wash time, $tw_2$, for said second, thin, sample being long enough to substantially, entirely remove all of said $C^{14}$ tagged gasoline molecules from said saturated second, thin, sample whereby said long wash time, $tw_2$, being in the range of about 8 to 12 hours; and c) said diffusion flow rate of said $C^{14}$-tagged gasoline molecules through said plastic solid is determined within a time range of about 10 hours to about 30 hours when said determinations of said quantities $c_o \cdot \sqrt{D}$ and $c_o$ are conducted sequentially.

22. Analytic method as in claim 21 wherein:

a) said solid is a two-layer solid having a first, thin, layer and a second, thick, layer, said first, thin, layer having a lower solubility than said second, thick, layer;

b) said first, thin, layer having a wetted surface and a mating surface, said wetted surface being exposed to said foreign fluid molecules, said mating surface being disposed to abut with a co-aligned mating surface of said second, thick, layer;

c) said second, thick, layer also having an ambient exposed surface;

d) said method comprising the additional steps of:

i) determining the saturation concentration, $c_o^1$, of said first, thin, layer in accord with the equation:

$$c_o^1 = \frac{c_o^2 \cdot S_1}{S_2}, \text{ where}$$

A) $c_o^2$ is the saturation concentration of said second, thick, layer, said saturation concentration, $c^2_o$, being ascertained in a manner consistent with the determination of $c_o$ for a homogenous solid;

B) S is the quantity of said foreign fluid molecule that diffuses into said wetted surface of said first, thin, layer;

C) $S_2$ is the quantity of said foreign fluid molecules that diffuses out of said air exposed surface of said second, thick, layer;

ii) determining the diffusion flow rate, dn/dt, per area of the two-layer solid in accord with the equation:

$$\frac{dn}{dt} = \frac{c_o^1 - D_2}{L}, \text{ where:}$$

A) $D_2$ is the diffusion constant of said second, thick, layer, said diffusion constant, $D_2$, being ascertained in manner consistent with the determination of D for a homogenous solid; and B) L is the thickness of said second, thick, layer.

23. Analytic method as in claim 22 wherein:

a) said first, thin, solid is a fluorinated coating;

b) said second, thick, solid is plastic; and c) said foreign fluid is gasoline.

24. Analytic method as in claim 22 wherein:

a) said first, thin, solid is a sulfonated coating;

b) said second, thick, solid is plastic; and c) said foreign fluid is gasoline.

* * * * *